United States Patent [19]
Sayama et al.

[11] Patent Number: 5,846,262
[45] Date of Patent: Dec. 8, 1998

[54] DISPOSABLE DIAPER

[75] Inventors: Yasushi Sayama; Yoshitaka Mishima, both of Kagawa-ken, Japan

[73] Assignee: Uni-Charm Corporation, Ehime-ken, Japan

[21] Appl. No.: 732,102

[22] Filed: Oct. 15, 1996

[30] Foreign Application Priority Data

Oct. 13, 1995 [JP] Japan .................................. 7-265795

[51] Int. Cl.⁶ .............................................. A61F 13/15
[52] U.S. Cl. ................................................... 604/391
[58] Field of Search ................................ 604/389–391

[56] References Cited

U.S. PATENT DOCUMENTS

| | | |
|---|---|---|
| 3,901,237 | 8/1975 | Cepuritis et al. . |
| 4,537,591 | 8/1985 | Coates ........................... 604/391 |
| 5,019,065 | 5/1991 | Scripps ........................... 604/391 |
| 5,049,145 | 9/1991 | Flug . |
| 5,053,028 | 10/1991 | Zoia et al. ........................... 604/391 |
| 5,476,702 | 12/1995 | Datta et al. ......................... 604/391 |
| 5,549,592 | 8/1996 | Fries et al. ......................... 604/391 |

FOREIGN PATENT DOCUMENTS

| | | |
|---|---|---|
| 0 563 457 | 10/1993 | European Pat. Off. . |
| 2 284 742 | 6/1995 | United Kingdom . |
| 83 03754 | 11/1983 | WIPO . |
| 96 27354 | 9/1996 | WIPO . |

*Primary Examiner*—Robert A. Clarke
*Attorney, Agent, or Firm*—Lowe, Price, LeBlanc & Becker

[57] ABSTRACT

A disposable diaper has a pair of hooked fastener components to detachably connect front and rear waist regions of the diaper. The hooked fastener components are bonded to transversely opposite sides, respectively, of the diaper rear waist region and are covered at transversely opposite side edges and/or vertically opposite end edges thereof with soft protective sheets, respectively, to prevent the wearer's skin from being irritated by the hooked fastener components.

9 Claims, 2 Drawing Sheets

DISPOSABLE DIAPER

BACKGROUND OF THE INVENTION

The present invention relates to a disposable diaper having front and rear waist regions adapted to be separably connected to each other in its actual use.

In disposable diapers, it is known to provide a pair of fastening zones on transversely opposite side edges of front or rear waist regions of the diaper so that these fastening zones may be peelably fastened to the other waist region in actual use of a diaper. It is also the commonly used technique to form such fastening zones by using a hooked fastener component or a looped fastener component constituting together a surface fastener which is known under the trademark of Velcro.

In such a diaper, the components of the surface fastener generally present a rigidity higher than the other parts of the diaper such as the topsheet and backsheet and this high rigidity sometimes irritates the baby's skin. In addition, the surface fastener component must be firmly bonded to the topsheet or backsheet in consideration of the fact that the surface fastener component of high rigidity bonded to the relatively soft topsheet or backsheet is repeatedly fastened to and peeled off from the outer surface of the diaper and a peeling force is generated on the interface between the soft sheet and the surface fastener component as the latter is peeled off from the outer surface of the diaper. However, such firm bonding increases the rigidity of the surface fastener component and irritation of the baby's skin due to the relatively sharp peripheral edge of the fastener component can become serious.

SUMMARY OF THE INVENTION

Accordingly, it is a principal object of the invention to provide an improved disposable diaper which allows both the peeling force acting on the peripheral edge of the surface fastener component and the skin stimulation due to the peripheral edge to be alleviated by covering the peripheral edge of the surface fastener component with a suitable sheet material.

The object set forth above is achieved, according to the invention, by a disposable diaper comprising a liquid-permeable topsheet, a liquid-impermeable backsheet and a liquid-absorbent core disposed between these two sheets, respective pairs of front and rear wings extending outward from transversely opposite sides of front and rear waist regions of the diaper, one of the pairs carrying a pair of hooked fastener components and the other pair carrying a pair of looped fastener components adapted to be separately interlocked with the hooked fastener components, the diaper being characterized by that each of the hooked fastener components is covered with a sheet which is more softer than the component except a middle zone and a zone extending aside to the front or rear waist regions.

DETAILED DESCRIPTION OF THE PREFERRED EMBODIMENT

Figure 1:
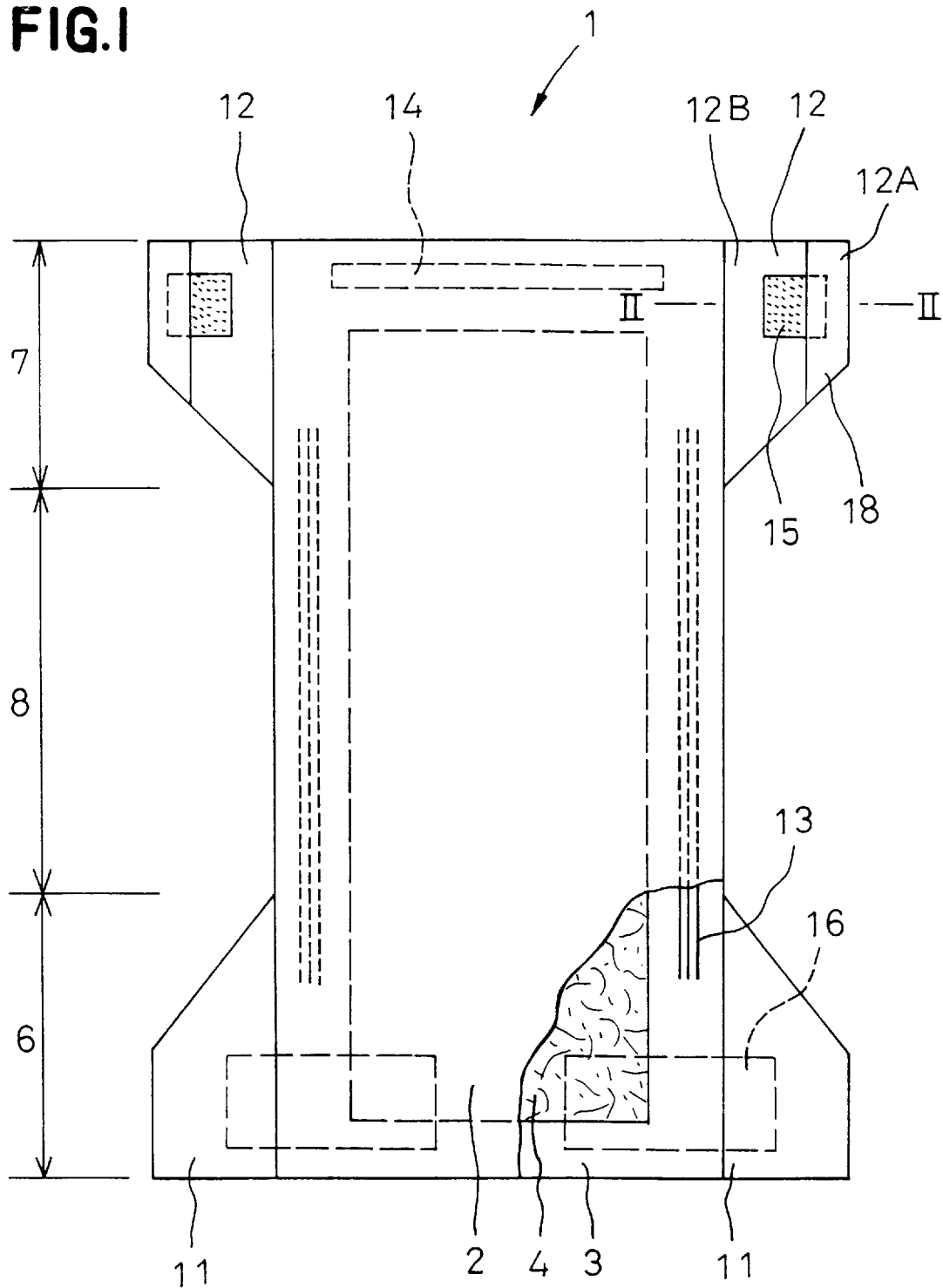
FIG. 1 is a plan view showing an embodiment of the inventive diaper as partially broken away.

A diaper 1 shown by FIG. 1 in a plan view as partially broken away comprises a liquid-permeable topsheet 2, a liquid-impermeable backsheet 3 and a liquid-absorbent core 4 disposed between these two sheets 2, 3. The diaper has a front waist region 6, a rear waist region 7 and a crotch region 8 extending between these two waist regions 6, 7. The front and rear waist regions 6, 7 are provided along their transversely opposite sides with front wings 11 and rear wings 12, respectively. The topsheet 2 and backsheet 3 are put one upon another over their portions extending outward beyond a peripheral edge of the core 4 and inner surfaces of these portions are water-tightly bonded together. The crotch region 8 is provided adjacent its transversely opposite side edges with elastic members 13 adapted to surround the baby's legs and the rear waist region 7 is provided adjacent its longitudinal end with an elastic member 14 extending along the waist line. These members 13, 14 are disposed between the topsheet 2 and backsheet 3 and secured in an elastically contractible condition to the inner surface of at least one of these two sheets 2, 3.

A hooked fastener component 15 having a plurality of hook elements, one component of the surface fastener commonly known under the trademark of Velcro, is integrally bonded to the inner surface of each rear wing 12 and a part of this hooked fastener component 15 extending laterally to an outer side edge 12A of the wing 12 has its inner surface covered with a protective sheet 18. A looped fastener component 16 having a plurality of loop elements, the other component of the surface fastener, is integrally bonded on its lower side to the outer surface of the front waist region and wing 6, 11.

Figure 2:
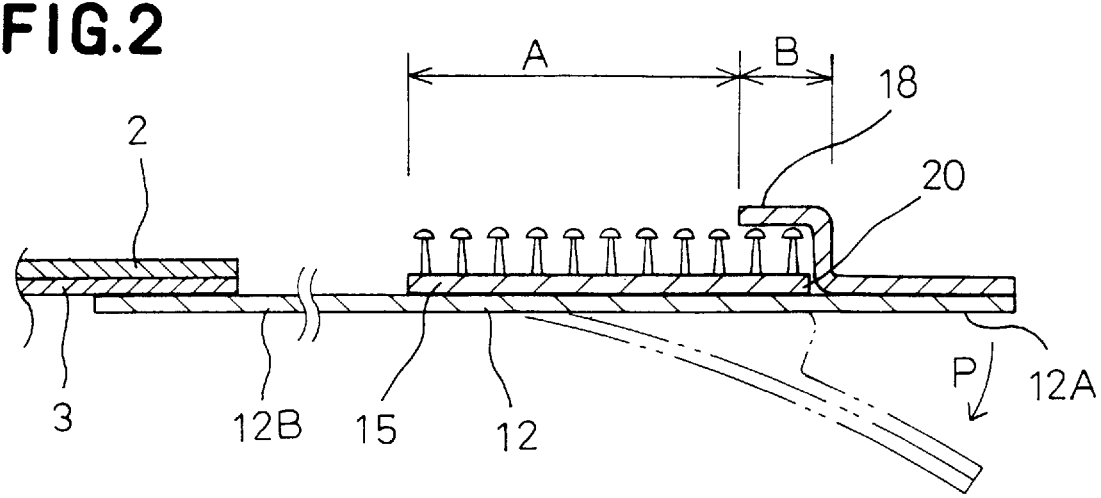
FIG. 2 is a sectional view taken along a line II—II in FIG. 1.

FIG. 2 is a sectional view taken along a line II—II in FIG. 1. As shown, an inner side edge 12B of each rear wing 12 is bonded to a side edge of the outer surface of the backsheet 3 and only a portion of the hooked fastener component 15 defined by a width A is exposed. The component 15 can be interlocked with the associated looped fastener component 16 on the front waist region 6 over a portion defined by the width A, i.e., a transversely middle zone as viewed in FIG. 3 and a zone extending inwardly aside to a middle line transversely dividing the diaper in two, but can not be interlocked with the component 16 over its outer portion defined by a width B and covered with the protective sheet 18. The hooked fastener component 15 once interlocked with the associated looped fastener component 16 may be pulled in the direction as indicated by an arrow P with the outer side edge 12A of the rear wing 12 being held by the user's fingers to peel off the portion defined by the width A starting from its right side, as indicated by the imaginary lines. In this state, so-called peeling force is practically in effective between the rear wing 12 and an outer edge 20 of the hooked fastener component 15, so the outer edge 20 is not easily peeled off from the rear wing 12. The outer edge 20 is covered with the protective sheet 18 and therefore does not irritate the wearer's skin.

Figure 3:
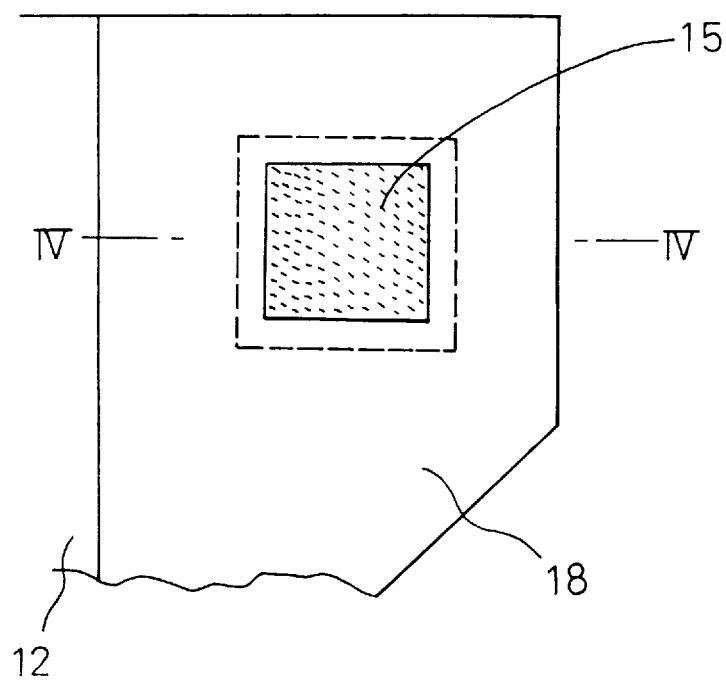
FIG. 3 is a fragmentary plan view showing an alternative embodiment of the inventive diaper.
Figure 4:
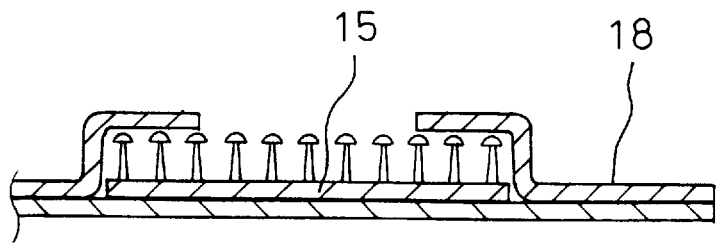
FIG. 4 is a sectional view taken along a line IV—IV in FIG. 3.

FIGS. 3 and 4 are respectively a fragmentary plan view showing an alternative embodiment of the inventive diaper 1 and a sectional view taken along a line IV—IV in FIG. 3. According to this embodiment of diaper 1, the hooked fastener component 15 of square shape has its peripheral edge entirely covered with the sheet 18 and is thus even less likely to irritate the wearer's skin than in the previously described embodiment in reference with FIGS. 1 and 2.

As the protective sheet 18 is used to alleviate skin irritation due to the hooked fastener component 15, it is preferred to employ, as this protective sheet 18, nonwoven fabric or plastic film which is less rigid than the component 15 and agreeable to the touch. The sheet 18 may be bonded to the inner surface of the rear wing 12 adjacent the peripheral edge of the component 15 and, if desired, the sheet 18 may be also bonded to the upper surface of the component 15.

Alternatively, the hooked fastener component 15 may be also implemented in the form of the conventional tape fastener laterally extending from the outer side edge 12A of the rear wing 12. In this case, the component 15 bonded to the inner surface of the tape strip will be covered with the protective sheet at least over its portion extending laterally to the outer side edge 12A of the wing 12.

To implement the inventive diaper 1, the front and rear wings 11, 12 may be formed by liquid-permeable or liquid-impermeable nonwoven fabric or plastic film. Alternatively, the topsheet 2 and/or the backsheet 3 may be laterally further extended to form the front and rear wings 11, 12. Bonding of the respective components or members may be achieved by use of adhesive, e.g., of hot melt type or by utilizing the heat-seal technique so far as a components or members to be bonded are a heat-sealable nature. It should be understood that no specific manner of such bonding is illustrated. While the looped fastener component 16 on the front body 6 is relatively soft and therefore not covered with the protective sheet 18 in the illustrated embodiment, the component 16 also may be covered with the protective sheet 18 similarly to the component 15, if it is desired.

The inventive disposable diaper effectively avoids an apprehension that the relatively sharp peripheral edge of the surface fastener components connecting the front and rear waist regions of the diaper in actual use might irritate the wearer's skin by covering the peripheral edge of the surface fastener components with the soft protective sheet. Such covering with the protective sheet is effective also to prevent the surface fastener components from being unintentionally peeled off from the diaper.

What is claimed is:

1. The disposable diaper comprising a liquid-permeable topsheet, a liquid-impermeable backsheet and a liquid-absorbent core disposed between these two sheets, respective pairs of front and rear wings extending outward from transversely opposite sides of front and rear waist regions of said diaper formed by said topsheet and backsheet, one of said pairs carrying a pair of hooked fastener components and the other pair carrying a pair of looped fastener components adapted to be separably interlocked with said hooked fastener components, wherein each of said hooked fastener components is partially covered with a sheet which is softer than said component.

2. The disposable diaper according to claim 1, wherein the sheet partially covering the hooked fastener components is not bonded or adhesively secured to the covered hooked components.

3. A disposable diaper, comprising:
a liquid-permeable topsheet;
a liquid-impermeable backsheet;
a liquid-absorbent core disposed between said topsheet and said backsheet to jointly define front and rear regions of the diaper and a crotch region therebetween;
pairs of front and rear wings respectively extending outward from transversely opposite sides of said front and rear regions;
a pair of hooked fastener components provided on an inner surface of said rear wings; and
a pair of looped fastener components provided on an outer surface of said front region for engagement with said hooked fastener components;
wherein each of said hooked fastener components is covered at transversely opposite side edges thereof with a protective sheet which is softer than said hooked fastener component.

4. The disposable diaper according to claim 3, wherein each of said hooked fastener components is covered at vertically opposite end edges thereof with said protective sheet.

5. The disposable diaper according to claim 3, wherein said protective sheet is made of a nonwoven fabric or plastic film.

6. The disposable diaper according to claim 3, wherein the sheet partially covering the hooked fastener components is not bonded or adhesively secured to the covered hooked components.

7. A disposable diaper, comprising:
a liquid-permeable topsheet;
a liquid-impermeable backsheet;
a liquid-absorbent core disposed between said topsheet and said backsheet to jointly define front and rear regions of the diaper and a crotch region therebetween;
pairs of front and rear wings respectively extending outward from transversely opposite sides of said front and rear regions;
a pair of hooked fastener components provided on an inner surface of said rear wings; and
a landing zone provided on an outer surface of said front region to be engaged with said hooked fastener components;
wherein each of said hooked fastener components is covered along entire peripheral edges thereof with a protective sheet which is softer than said hooked fastener component.

8. The disposable diaper according to claim 7, wherein said protective sheet is made of a nonwoven fabric or plastic film.

9. The disposable diaper according to claim 7, wherein the sheet partially covering the hooked fastener components is not bonded or adhesively secured to the covered hooked components.

* * * * *